US005750126A

United States Patent [19]
Smith et al.

[11] Patent Number: 5,750,126
[45] Date of Patent: May 12, 1998

[54] LABILE INSECTICIDE COMPOSITIONS

[75] Inventors: Kelly L. Smith; Scott H. Herbig, both of Bend, Oreg.

[73] Assignee: Bend Research, Inc., Bend, Oreg.

[21] Appl. No.: 584,986

[22] Filed: Jan. 11, 1996

Related U.S. Application Data

[63] Continuation of Ser. No. 189,905, Feb. 1, 1994, abandoned.

[51] Int. Cl.⁶ .................................................. A01N 25/28
[52] U.S. Cl. .......................... 424/405; 424/408; 424/409; 424/497
[58] Field of Search .................................. 424/405, 408, 424/409, 497

[56] References Cited

U.S. PATENT DOCUMENTS

| | | | |
|---|---|---|---|
| 3,541,203 | 11/1970 | Fogle et al. | 424/84 |
| 4,948,586 | 8/1990 | Bohm et al. | 424/406 |
| 4,985,449 | 1/1991 | Haga et al. | 514/349 |
| 5,141,744 | 8/1992 | Chang et al. | 424/93 |

FOREIGN PATENT DOCUMENTS 2109687  6/1983  United Kingdom .................. 424/408

Primary Examiner—Neil S. Levy
Attorney, Agent, or Firm—Chernoff, Vilhauer, McClung & Stenzel, LLP

[57] ABSTRACT

There is disclosed a pesticidal composition comprising a pH-sensitive non-lignin-based polymer encapsulating both the active agent and a lignin-based UV screening agent.

6 Claims, No Drawings

LABILE INSECTICIDE COMPOSITIONS

This is a continuation of application 08/189,905 filed on Feb. 1, 1994 now abandoned.

The government has a nonexclusive, nontransferable, royalty-free license to practice certain aspects of this invention under Contract No. 90-33610-5794 awarded by the United States Department of Agriculture.

BACKGROUND OF INVENTION

This invention relates to labile insecticide compositions, wherein the insecticides are protected from environmental degradation, yet still provide superior insecticidal activity following ingestion by the insect.

Some insecticides, especially labile biological insecticides which become active upon ingestion by the target insect, have a very short effective lifetime in the field. They are typically degraded within a few hours or days by ultraviolet (UV) light, by oxygen, or by dehydration. This short effective lifetime severely restricts the usefulness of such insecticides. These insecticides are typically effective against the larval forms of the target insect, and they must be present when the larvae are feeding. If such insecticides are applied much before the larvae are present, they are degraded before the larvae arrive, and the larvae are unaffected. Of course, if such insecticides are applied too late, the insect larvae have already caused significant damage to the crop. Thus, absent a method for preserving their efficacy, biological insecticides must be applied at precisely the correct time.

Labile insecticides often have substantial advantages over conventional insecticides. They typically have very low toxicity to nontarget organisms, and are thus safer and more selective than are conventional insecticides. It is therefore clear that increasing the stability of such labile insecticides is a desirable objective in pest control. Several attempts have been made over the last 25 years to improve the stability of biological insecticides in particular.

For example, various researchers have attempted to improve stability of bacterial and viral insecticides by adding UV absorbers, such as dyes, pigments, carbon black, benzophenones, benzimidazoles, lignin derivatives, and fluorescent whitening agents. Martignoni et al., 78 *J. Econ. Entomol.* 982 (1985). In general, such approaches have suffered from an inability to maintain close contact between the UV absorber and the labile insecticide.

A principal advance in the art was made by Fogle and Peyton who demonstrated the advantages of combining light-absorbing materials with a polymeric binder to maintain close contact of the UV absorber with the insecticide. In their U.S. Pat. No. 3,541,203, there is described an insecticidal virus formulation comprising a *Heliothis virescens* virus and a light-absorbing material of either carbon or aluminum particles, both enclosed within a polymeric binder of cellulose acetate phthalate.

Similarly, Ignoffo et al., in 64 *J. Econ. Entomol.* 850 (1971) disclosed microencapsulated *Heliothis virescens* nuclear polyhedrosis virus comprising virus particles, a polymeric encapsulating material consisting of either gelatin or ethylcellulose, and a light absorber consisting of carbon, aluminum, or aluminum oxide. Bull et al., in 69 *J. Econ. Entomol.* 731 (1976) disclosed formulations of the same virus combined with digestible, water-insoluble polymers and either titanium dioxide or carbon black as light-absorber. The polymers used were either polyvinylalcohol or styrene maleic anhydride half ester. More recently, Dunkle et al., in 17 *Envir. Entomol.* 120 (1988) disclosed *Bacillus thuringiensis* encapsulated in a starch matrix.

U.S. Pat. Nos. 4,844,896 and 4,948,586 disclose viral, bacterial, or fungal pathogens coated with pH-sensitive polyacrylates and containing various dyes and other conventional light-absorbing materials. PCT Application No. 89/07447 discloses bacteria coated with polymers (dextran, starch, gelatin, alginate, carrageenan, chitosan, or polyoxyethylene bis amine) that are permeable to insect digestive enzymes at alkaline pH. PCT Application No. 92/19102 discloses biological insecticides encapsulated with lignins or lignin derivatives. U.S. Pat. No. Re 29,238 also discloses the encapsulation of herbicides by lignin.

The principal drawback of each of the foregoing encapsulated pesticides is that their effective life is too short. A lignin-encapsulated pesticide suffers from the additional drawback that the active biological agent leaches out in an aqueous environment and then becomes susceptible to breakdown by UV radiation.

Although each of the foregoing developments may be characterized as an advance in the state of the art, there continues to be a need for formulations of labile pesticides that have improved stability and resistance to UV radiation. This need and others are met by the present invention, which is summarized and described in detail below.

SUMMARY OF THE INVENTION

The present invention comprises an improved formulation of labile pesticides. The formulation comprises particles containing the active ingredient (pesticide), a non-lignin-based pH-sensitive polymeric material, and a lignin-based light-absorbing material. The pH-sensitive polymer encapsulates both the active ingredient and the lignin-based light-absorbing material together in each particle, thus allowing the light-absorbing material to protect the pesticide from light. A significant advantage of the use of lignin-based light-absorbing material is that such material is environmentally safe and there are currently no limitations on the allowable percentages in agricultural formulations, as is the case with many other light-absorbing materials. The encapsulating polymer maintains the light-absorbing material in close contact with the active ingredient until it is exposed to an alkaline environment, such as is found in the gut of an insect. The polymer then dissolves, releasing the active ingredient to the insect gut. The pH-sensitive polymer may be blended with a non-pH-sensitive polymer to increase strength, coatability, or other desirable properties.

DETAILED DESCRIPTION OF PREFERRED EMBODIMENTS

The composition of the present invention comprises active ingredient (ai) and a lignin-based light-absorbing material, the ai and the light absorbent both being encapsulated together by a non-lignin-based pH-sensitive polymer. The ai is typically present in the form of solid particles, which may be present in a mixture of other solid particles. Such is typically the case, for example, with active ingredients produced by fermentation or by in vivo culturing; in these cases, fermentation media, nutrients, insect parts, etc. are also present. In the encapsulated pesticidal composition of the present invention, the solids containing the ai (except for viruses) preferentially comprise from 20 to 80 wt % of the encapsulated particle, and more preferably, from 30 to 70 wt %. For viruses, the solids containing the virus preferentially comprise from 0.1 to 15 wt % of the encapsulated particle, and more preferably, from 1 to 5 wt %.

The lignin-based light-absorbing material preferentially comprises from 15 to 60 wt % of the encapsulated particle for non-virus-containing active ingredients, and more preferably from 15 to 40 wt %. For virus-containing active ingredients, the lignin-based light-absorbing material preferentially comprises from 20 to 60 wt % of the encapsulated particle, and more preferably from 30 to 60 wt %. Such high percentages are allowable under U.S. Environmental Protection Agency (EPA) regulations. The pH-sensitive polymer preferentially comprises from 10 to 40 wt % of the encapsulated particle for non-virus-containing active ingredients and from 20 to 80 wt % of the encapsulated particle for virus-containing active ingredients.

Labile insecticides for which this invention is particularly useful are those that are degraded by sunlight, including bacterial insecticides, viral insecticides, fungal insecticides, protozoans, avermectins, and milbemycins. In addition, insect growth regulators that are not stable in the presence of UV radiation are useful in this invention.

Examples of bacterial insecticides include *Bacillus thuringiensis* varieties: israelensis, kurstaki, berliner, san diego, aizawa, galleriae, morrisoni, tenebrionis, tolworthi, darmstadiensis, and kyushiensis; *Bacillus sphaericus*; *Bacillus popilliae*; and other bacteria that are pathogenic to target insects or other target organisms. In most cases, the pesticidal ai is a protein endotoxin produced by the bacteria, rather than the bacteria itself, and preparations of bacterial pesticide must contain the endotoxin.

Examples of viral insecticides are the baculoviruses, including nuclear polyhedrosis viruses (NPVs), granulosis viruses, and nonoccluded baculoviruses. Examples of NPVs are *Heliothis zea* NPV, *Autographa californica* NPV, *Anagrapha falcifera* NPV, *Spodoptera frugiperda* NPV, *Trichoplusia ni* NPV, *Anticarsia gemmatalis* NPV, *Orgyia pseudotsugata* NPV, *Lymantria dispar* NPV, *Neodiprion sertifer* NPV, and *Christoneura fumiferana* NPV. Examples of granulosis viruses include *Cydia pomonella* (codling moth) granulosis virus, *Agrotis segetum* granulosis virus, *Erinnyis ello* granulosis virus, and *Pieris rapae* granulosis virus. An example of nonoccluded baculoviruses is *Oryctes rhinoceros* baculovirus.

Fungi typically invade insects through a cuticular route; however, infection can occur by ingestion, as well. Examples of insecticidal fungi include *Aschersonia aleyrodis*, *Beauveria bassiana*, *Hirsutella thompsonii*, *Metarhizium anisopliae*, *Verticilllium lecanji*, *Conidiobolus obscurus*, *Erynia neoaphidis*, *Erynia radicans*, *Beauveria brongnartii*, *Paecilomyces fumoso-rosea*, *Hirsutella citriformis*, *Metarhizium flavoviride*, *Nomuraea rileyi*, and *Paecilomyces lilacinus*.

Protozeans useful for insect control include flagellates, ciliates, amoebae, coccidia, haplosporida, neogregarines, and microsporida. Of particular importance are the microsporida in the genus Nosema, e.g., *Nosema locustae*.

Avermectins and milbemycins are pesticides derived from Streptomyces species of soil-inhabiting microorganisms. Examples of avermectins are A1a, A2a, B1a, B2a, A1b, A2b, B1b, B2b, and derivatives and mixtures of these, such as Ivermectin and abamectin. Examples of milbemycins are a1, a2, b1, b2, D, and derivatives and mixtures of these.

Examples of insect growth regulators include juvenile hormone analogs such as methoprene, kinoprene, hydroprene, triprene, epofenonane, and fenoxycarb; anti-juvenile hormone analogs such as precocene, ponasterone A, benzodioxoles, and ecdysone; and chitin synthesis inhibitors such as diflubenzuron, chlorfluazuron, buprofezin, penfluron, teflubenzuron, and trifluron.

The non-lignin-based pH-sensitive polymer maintains the light-absorbing material in close contact with the ai until it is exposed to an alkaline pH, such as is found in the gut of an insect. Typically, the pH-sensitive polymers are insoluble solids in neutral or acidic aqueous solutions, and then they dissolve at least partially at pH above about 5 to 9. They may be blended with other pH-sensitive polymers or with non-pH-sensitive polymers, so long as the latter are not lignin-based.

Examples of encapsulating polymers useful in the invention include polyacrylamides, phthalate derivatives (i.e., compounds with covalently attached phthalate moieties) such as acid phthalates of carbohydrates, cellulose acetate phthalate, amylose acetate phthalate, other cellulose ester phthalates, cellulose ether phthalates, methylcellulose phthalate, hydroxypropylmethylcellulose phthalate, hydroxypropylcellulose phthalate, hydroxypropylethylcellulose phthalate, polyvinyl acetate phthalate (PVAP), polyvinyl acetate hydrogen phthalate, sodium cellulose acetate phthalate, starch acid phthalate, styrene-maleic acid dibutyl phthalate copolymer, and styrene-maleic acid polyvinyl acetate phthalate copolymer, styrene and maleic acid copolymers, formalized gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, vinyl acetate and crotonic acid copolymers, acrylic and methacrylic acids, their esters and copolymers thereof.

Preferred encapsulating polymers are inexpensive film-forming polymers that are stable at pH less than 7 and are soluble at pH greater than 10. These include shellac, cellulose acetate phthalate (CAP), polyvinyl acetate phthalate (PVAP), vinyl acetate and crotonic acid copolymers, and acrylic and methacrylic acids, their esters and copolymers thereof.

The non-lignin-base pH-sensitive polymer may be blended with a non-lignin-based non-pH-sensitive polymer to provide increased strength, coatability, or other desirable properties. Suitable non-pH-sensitive polymers are those that are soluble in the same solvent used to dissolve the pH-sensitive material and that impart the desired characteristics to the final product. Such non-pH--sensitive polymers include cellulose derivatives such as cellulose acetate, cellulose acetate butyrate, cellulose acetate propionate, or ethyl cellulose, polysulfones, polycarbonates, polyurethanes, polyvinylacetates, polyvinyl alcohols, polyesters, polyalkenes, polystyrenes, polyacrylic acid derivatives such as polyacrylates, polymethylmethacrylate, polyethylmethacrylate, and polyacrylic acid esters with higher alkyl groups, polyamides, polyethers, and waxes such as beeswax, candelilla wax, carnauba wax, Jojoba wax, petroleum wax, polyethylene wax, paraffin wax, microcrystalline wax, and the like.

Lignin-based light-absorbing materials are advantageous for three reasons: (1) they are effective light-absorbing agents as they have been approved by the U.S. EPA for use in high concentrations, (2) they are effective dispersants, which aids in preventing agglomeration of the particles, and (3) they are inexpensive, which allows their economical use at high concentrations in agricultural products. Examples of lignin-based light-absorbing materials include Kraft-derived lignins, alkali lignin sulfonates and derivatives thereof, such as sodium lignin sulfonate, calcium lignin sulfonate, sodium-calcium lignin sulfonate, calciummagnesium lignin sulfonate, oxidized sodium lignin sulfonate, carboxylated sodium lignin sulfonate, partially desulfonated lignin sulfonate, ammonia lignin sulfonate, or alkali lignin sulfonate.

The improved formulations of the present invention can be prepared by a number of coating processes, including spray-drying, spray-coating, fluid-bed coating, pan-coating, spray-chilling, thermal phase inversion, and the like. They are preferably prepared by a spray-dry coating process. In this process, small particles of the ai are mixed with the lignin-based material in a solution of the pH-sensitive polymer in a solvent, forming a slurry that is fed directly to an atomizing spray nozzle. The slurry is sprayed from the nozzle into a drying chamber where the solvent evaporates from the polymer solution, causing the polymer to precipitate, forming a protective coating around small particles of the ai and of the lignin-based light-absorbing agent. Each coated particle contains particles of the pesticidal ai and the lignin-based light-absorbing material, held together and coated with the pH-sensitive polymer. These coated particles are collected as a free-flowing powder by conventional means.

This process is similar to conventional spray-drying operations, except that the droplet concentration in the drying chamber is low to minimize agglomeration. An additional difference is that the final particle size (typically 5–20 microns) is much smaller than those typically seen in spray-drying fabrication techniques (usually larger than 300 microns in diameter). A further difference is that this process allows the pesticidal ai to be mixed with the polymer solution just prior to entering the spray nozzle, allowing very short times for exposure of the labile pesticidal ai to the solvent system, and ensuring better retention of activity of the ai.

This type of spray-dry coating process is inexpensive and can easily be scaled to large volumes. In addition, it is amenable to addition of other ingredients to the pesticidal formulation, such as feeding stimulants, anti-oxidants, surfactants, dispersants, and the like. A further advantage of this spray-dry coating process relates to the typical fermentation processes used to produce many of the pesticidal active ingredients. That is, the pH-sensitive polymer and lignin-based light-absorbing material can be added directly to the aqueous fermentation concentrate containing the pesticidal ai, and this mixture can then be spray-dried. This eliminates the typical step of spray-drying the ai first, and then mixing it with a polymer solution to coat by a second spray-drying operation.

EXAMPLE 1

Polymer-encapsulated formulations of a pesticidal ai comprising the celery looper (*Anographa falcifera*) nuclear polyhedrosis virus (AfNPV) were prepared according to the present invention using the following procedure. Eudragit S-100 acrylic acid-methacrylic acid copolymer (Rohm Pharma, Germany) and lignin-based light-absorbing material ("lignin") were added to a mixture of 87% acetone and 13% water and stirred for several hours to dissolve the Eudragit pH-sensitive polymer. Two different lignins were used: Indulin AT (Westvaco, Charleston Heights, S.C.), which is a pH-sensitive, relatively water-insoluble lignin; and D-435-1 (Lignotech, Rothschild, Wis.), which is not pH-sensitive, and is a relatively water-soluble lignin. A suspension of AfNPV containing $4.5 \times 10^9$ polyinclusion bodies (PIB) per gram was added to the Eudragit/lignin mixture just prior to spraying. The resulting suspension was pumped through a peristaltic pump at a rate of 50 mL/min to a two-fluid spray nozzle, which atomized the liquid suspension with air into the top of a drying chamber approximately 1 m in diameter by 4 m in height. The drying chamber was maintained at room temperature, which allowed the solvent to evaporate, solidifying the particles before they reached the bottom of the chamber. The solidified particles, comprising lignin and the pesticidal ai AfNPV together encapsulated by Eudragit, were collected using a cyclone separator attached to the bottom of the chamber.

For comparison, lignin-encapsulated particles of the type described in PCT Application No. 92/19102 were prepared using the same pH-sensitive polymer (Eudragit S-100) and Indulin AT as the lignin in the same manner as described in Example 1 of that document, with the exception that AfNPV, instead of Amdro, was used as the ai. The preparation of encapsulated particles by the same method using the more-water-soluble lignin D435-1 was also attempted. Under the pH conditions present, the D435-1 lignin does not precipitate and so would be incapable of encapsulating the ai; thus, to the extent any ai is encapsulated, the encapsulation must be by the Eudragit polymer. This attempt was unsuccessful, however, as no encapsulation of ai particles was observed, indicating that the polymer is not the encapsulating material in the method disclosed in PCT Application No. 92/19102.

To determine the structure of the encapsulation in each case, all three sets of the particles prepared by the two methods described above were leached with distilled water in an effort to dissolve the lignin without dissolving the polymer. To do this, 25 mg of particles were placed into 1 liter of distilled water and stirred continuously for 110 hours. Samples of the water were then filtered through a 5 μm filter. Lignin leached from the particles was measured by spectrophotometric analysis and the number and size of particles remaining after leaching were determined by scanning electron microscopy (SEM).

The formulations prepared and the results obtained from leaching are shown in the table below. The polymer-encapsulated formulations prepared according to the present invention lost 6.2% and 23.2% of the lignin during leaching; however, there were no particles lost to leaching. That is, all the particles remained intact and were large enough to be retained on the filter. This means that the polymer, rather than the lignin, was the encapsulating material, and it encapsulated both the ai and the lignin. Particles examined by SEM before and after leaching had the same appearance, with no apparent porosity in the surface, further evidencing that both the ai and the lignin particles were encapsulated by the polymer.

In contrast, the lignin-encapsulated formulation prepared according to PCT 92/19102 lost 9.0% of the lignin during leaching, but, due to loss of lignin binding agent through leaching, 90% of the particles either dissolved or were sufficiently reduced in size to pass through the filter. This particle loss is consistent with the lignin being the encapsulating material, rather than the polymer; if the polymer had been the encapsulating agent the particles would have remained about the same size and would have been retained on the filter.

| Formulation | Polymer Content (wt %) | Lignin Content (wt %) | ai Content (wt %) | Lignin Lost to Leaching (%) | Particle Loss (%) |
|---|---|---|---|---|---|
| Eudragit/ Indulin* | 19.8 | 79.4 | 0.8 | 6.2 | 0 |
| Eudragit/ D-435-1* | 19.8 | 79.4 | 0.8 | 23.2 | 0 |
| Eudragit/ Indulin** | 20.8 | 78.4 | 0.8 | 9.0 | 90 |

*Prepared according to the present invention.
**Prepared according to PCT Application No. 92/190102.

EXAMPLE 2

A polymer-encapsulated formulation of the pesticidal ai codling moth (*Cydia pomonella*) granulosis virus (CMGV)

was prepared according to the present invention by the following procedure. The polymer and lignin were added to a mixture of 75% acetone and 25% water and stirred for several hours to dissolve the polymer. The standard CMGV suspension contained approximately $2 \times 10^{12}$ PIB per gram and about 7 wt % solids; this suspension was centrifuged to obtain approximately 40 wt % solids. Just prior to spraying, the CMGV suspension was added to the polymer solution. The resulting suspension was sprayed through the same type of nozzle into a drying chamber as in Example 1. The encapsulating polymer used was Eudragit S-100, and the lignin was Orzan LS, a sodium lignin sulfonate (ITT Rayonier, Hoquiam, Wash.). The encapsulated formulation contained 13 wt % CMGV and 29 wt % Orzan.

For comparison, polymer-encapsulated formulations of CMGV were also prepared by the same method without any lignin light-absorbing material and with light-absorbing materials other than lignins. Two common non-lignin light-absorbing materials were used at the highest level allowed by the U.S. EPA for use on crops (4 wt %): (1) a benzotriazole, Tinuvin 328 (Ciba Geigy Corp., Hawthorne, N.Y.); and (2) a benzophenone, Hostavin AR08 (Hoechst Celanese Corp., Somerville, N.J.). Each of these formulations also contained 13 wt % CMGV.

The viral formulations described above were evaluated for their efficacy against codling moth larvae. The formulations were placed onto nutrient-containing media and exposed to neonate codling moth larvae after varying lengths of exposure to UV light, and the resulting mortality of the larvae was determined. As shown in the following table, the formulations containing light-absorbing material exhibited higher mortalities than did the polymer-encapsulated formulation with no light-absorbing material. It is also clear that the formulation containing lignin as the light-absorbing material performed better than did the formulations containing the common non-lignin light-absorbing materials.

| Formulation by Wt % | % Mortality After 0.5 hr UV Exposure | % Mortality After 1 hr UV Exposure | % Mortality After 3 hr UV Exposure |
|---|---|---|---|
| 58 Eudragit, 29 Orzan, 13 CMGV | 100 | 93 | 50 |
| 87 Eudragit, 13 CMGV | 53 | nm | 10 |
| 83 Eudragit, 4 Tinuvin, 13 CMGV | 70 | 37 | 40 |
| 83 Eudragit, 4 Hostavin, 13 CMGV | 97 | 78 | 30 | nm = not measured

EXAMPLE 3

A polymer-encapsulated formulation of the pesticidal ai *Bacillus thuringiensis* (Bt) was prepared in substantially the same manner as set forth in the first paragraph of Example 1. The encapsulating polymer and lignin were added to pure acetone and stirred for several hours to dissolve the encapsulating pH-sensitive polymer. Just prior to spraying, the Bt was added to the Eudragit/lignin mixture. The resulting suspension was sprayed and the encapsulated particles collected as in Example 1. The encapsulating polymer used was Eudragit S-100, and the lignin Orzan LS. The formulation contained 40 wt % Bt, 40 wt % Eudragit, and 20 wt % Orzan.

For comparison, polymer-encapsulated formulations of Bt were also prepared by the same method without any lignin light-absorbing material and with light-absorbing materials other than lignins. The non-lignin light-absorbing materials used were a benzophenone and a neutralized organic acid, both obtained from Ecogen Inc. (Langhorne, Pa.), and they were used in the concentrations suggested by the manufacturer and allowed under U.S. EPA regulations.

The activity of the Bt formulations was evaluated for resistance to UV light degradation of the bacteria, as reflected in the amount of endotoxins present. The formulations were exposed to UV light for one hour, and their pesticidal activity was measured by determining the percentage of the initial amount of Bt protein endotoxins remaining. The results are shown in the table below. As may be seen, the formulation containing the lignin (Orzan) as the light-absorbing material was substantially more effective in maintaining its pesticidal activity upon exposure to UV light than were the formulations containing both no light-absorbing materials and non-lignin light-absorbing materials.

| Formulation by Wt % | Endotoxin Cry IA Remaining (%) | Endotoxin Cry II Remaining (%) |
|---|---|---|
| 40 Eudragit, 20 Orzan, 40 Bt | 82 | 98 |
| 75 Eudragit, 25 Bt | 30 | 56 |
| 73 Eudragit, 0.2 Benzophenone, 26.8 Bt | 38 | 59 |
| 71 Eudragit, 4 Neutralized Organic Acid, 25 Bt | 53 | 68 |

EXAMPLES 4–20

Coated formulations of *Bacillus thuringiensis* (Bt) were prepared using the following procedure. The polymer and lignin-based light-absorbing material ("lignin") were added to acetone and stirred for several hours to dissolve the polymer. Just prior to spraying, the Bt was added to the polymer/lignin mixture. The resulting suspension was pumped through a peristaltic pump at a rate of 50 mL/min to a two-fluid spray nozzle, which atomized the suspension into the top of a drying chamber approximately 1 m in diameter by 4 m in height. The drying chamber was maintained at ambient temperature, which allowed the particles to precipitate before they reached the bottom of the chamber. The precipitated particles, comprising lignin and ai together and encapsulated by polymer, were collected using a cyclone separator attached to the bottom of the chamber. The formulations of Examples 4–20 were coated in this manner.

In these examples, PVAP E-735 is polyvinyl acetate phthalate (Colorcon, West Point, Pa.); CAP is cellulose acetate phthalate (Eastman Chemicals, Kings-port, Tenn.); Vinac refers to Vinac ASB-516, a copolymer of vinyl acetate and crotonic acid (Air Products, Allentown, Pa.); shellac was obtained from Colony Import and Export Corp., Garden City, N.Y.; Carboset refers to Carboset 514A, an acrylic acid ethyl acrylate copolymer (B. F. Goodrich, Cleveland, Ohio); Orzan refers to Orzan LS, a sodium lignin sulfonate (ITT Rayonier, Hoquiam, Wash.), D-435-1 and D-435-2 are sodium lignin sulfonate and alkali lignin sulfonate, respectively (Lignotech, Rothschild, Wis.); and Indulin® refers to Indulin® AT, a purified form of Kraft lignin (Westvaco, Charleston Heights, S.C.).

| Ex No | Polymer | wt % Polymer | Type Lignin | wt % Lignin | wt % Bt | Total wt % Solids |
|---|---|---|---|---|---|---|
| 4 | PVAP E-735 | 50 | Orzan | 25 | 25[2] | 10[1] |
| 5 | PVAP E-735 | 50 | " | 25 | 25 | 10[1] |
| 6 | PVAP E-735 | 50 | " | 25 | 25 | 10[3] |
| 7 | PVAP E-735 | 40 | " | 20 | 40 | 15[4] |
| 8 | CAP | 50 | " | 25 | 25 | 10[1] |
| 9 | " | 40 | " | 20 | 40 | 10[1] |
| 10 | " | 40 | D-435-1 | 20 | 40 | 10[1] |
| 11 | " | 40 | D-435-1 | 20 | 40 | 10[1] |
| 12 | Vinac | 40 | Orzan | 20 | 40 | 10[1] |
| 13 | " | 40 | D-435-1 | 20 | 40 | 10[1] |
| 14 | " | 40 | D-435-2 | 20 | 40 | 10[1] |
| 15 | Shellac | 50 | Orzan | 25 | 25 | 20[5] |
| 16 | " | 40 | " | 20 | 40 | 15[6] |
| 17 | " | 40 | " | 20 | 40 | 15[7] |
| 18 | " | 30 | " | 10 | 60 | 15[4] |
| 19 | " | 40 | " | 20 | 40 | 44[8] |
| 20 | Carboset[9] | 31 | Indulin ® | 29 | 40 | 10[10] |

[1] in acetone
[2] Bt was added in the form of an aqueous slurry containing about 12% Bt
[3] in 84% acetone and 16% water
[4] in 67% acetone and 33% water
[5] in ethanol
[6] in methanol
[7] in tetrahydrofuran
[8] in 83% ethanol and 17% water
[9] includes 2% polyvinylpyrrolidone
[10] in 80% acetone and 20% water

EXAMPLES 21–24

Encapsulated formulations of Bt were prepared as in Example 1 except that the Bt and Orzan were dispersed in an aqueous suspension (12% solids) and the PVAP was dissolved in acetone (approximately 7% solids); these two liquids were then mixed just prior to spraying.

| Ex. No. | Polymer | wt % Polymer | Type Lignin | wt % Lignin | wt % Bt | Total wt % Solids[1] |
|---|---|---|---|---|---|---|
| 21 | PVAP E-735 | 36 | Orzan | 19 | 25 | 11[2] |
| 22 | PVAP E-735 | 40 | " | 20 | 20 | 11[2] |
| 23 | PVAP E-735 | 50 | " | 25 | 25 | 8 |
| 24 | PVAP E-735 | 60 | " | 30 | 10 | 7 |

[1] in water
[2] also contained 1 wt % ammonium hydroxide and 20 wt % molasses

EXAMPLES 25–37

Encapsulated formulations of Codling Moth granulosis virus (CMGV) were prepared using the following procedure. The polymer and lignin-based light-absorbing material ("lignin") were added to a mixture of 75% acetone and 25% water and stirred for several hours to dissolve the polymer. In Examples 31, 34 and 35 the formulation also contained Hostavin ARO-8, a benzophenone light-absorbing agent (Hoechst Celanese, Somerville, N.J.). The CMGV (as either a standard ("std") preparation containing approximately $2 \times 10^{12}$ polyinclusion bodies (PIB) per gram and about 7 wt % solids, or as a larval ("larva") preparation containing approximately $5 \times 10^{13}$ PIB per gram and about 14 wt % solids) was centrifuged to obtain approximately 40 wt % solids. Just prior to spraying, the CMGV was added to the polymer solution. The resulting suspension was sprayed through a nozzle and the encapsulated particles collected as in Example 1.

| Ex. No. | Polymer | Wt % Polymer | Type Lignin | Wt % Lignin | Type Virus | Wt % Virus | Wt % Total Solids |
|---|---|---|---|---|---|---|---|
| 25 | PVAP | 58 | Orzan | 29 | std | 13 | 10[1] |
| 26 | " | 55 | " | 27 | " | 18 | 8[2] |
| 27 | " | 40 | " | 20 | " | 40 | 12[1] |
| 28 | " | 65 | " | 33 | larv | 3 | 10[1] |
| 29 | " | 66 | " | 33 | " | 1 | 10[1] |
| 30 | " | 50 | " | 10 | std | 20 | 10[3] |
| 31 | " | 40 | " | 20 | " | 40 | 10[4] |
| 32 | " | 50 | " | 16 | " | 2 | 10[3] |
| 33 | " | 64 | " | 32 | " | 3 | 10[1] |
| 34 | Shellac | 60 | " | 22 | " | 18 | 8[4] |
| 35 | " | 40 | " | 20 | " | 40 | 8[5] |
| 36 | " | 40 | " | 20 | " | 40 | 9[6] |
| 37 | Vinac | 50 | " | 25 | " | 25 | 8[1] |

[1] in acetone
[2] in 18 wt % water and 82 wt % acetone
[3] also contained 10 wt % methylcellulose and 10 wt % sucrose
[4] also contained 0.2 wt % Hostavin
[5] also contained 0.1 wt % Hostavin
[6] in 95% ethanol and 5% water

EXAMPLES 38–39

Encapsulated formulations of AfNPV were prepared as in the first paragraph of Example 1. The pH-sensitive polymers used were either Vinac ASB-516 or Carboset 514A. The lignin used was Indulin AT. The compositions of the formulations are listed in the table below.

| Ex. No. | Polymer | Wt % Polyler | Wt % Lignin | Wt % Virus | Wt % Total Solids |
|---|---|---|---|---|---|
| 38 | Vinac | 49.6 | 49.6 | 0.8 | 9.3 |
| 39 | Carboset | 49.6 | 49.6 | 0.8 | 9.3 |

EXAMPLE 40

Bt formulations from Examples 4, 5, 9, 16 and 22–24 were evaluated in laboratory bioassay tests for their efficacy against beet armyworm larvae, a common insect pest, as compared to the efficacy of uncoated Bt. In these tests, the initial efficacy was measured as the concentration of formulation required to cause 50% mortality of the larvae. The protection provided by a number of the encapsulated formulations against UV degradation was also determined, by measuring the percentage of Bt protein endotoxins (IA and II) remaining after UV exposure of various periods of time. Following are the results of the bioassay tests.

| Ex. No. | Initial Efficacy (ng/unit) | % Endotoxin Remaining After UV Exposure | | | | | |
|---|---|---|---|---|---|---|---|
| | | 1 hr | | 2 hr | | 3 hr | |
| | | IA | II | IA | II | IA | II |
| * | 100–300 | 50 | 85 | 0 | nm | 0 | nm |
| 4 | 238 | nm | nm | nm | nm | nm | nm |
| 5 | 142 | 88 | 91 | 41 | 64 | nm | 67 |
| 22 | 644 | 89 | 93 | nm | nm | nm | nm |
| 23 | 154 | 79 | 73 | nm | nm | nm | nm |
| 24 | 333 | nm | nm | nm | nm | nm | nm |
| 9 | nm | nm | nm | 41 | 62 | 27 | 55 |
| 16 | 114 | 66 | 62 | 54 | 62 | 23 | 45 |

* = uncoated Bt

Thus, the encapsulated formulations exhibited comparable initial efficacy and substantially improved protection against UV degradation.

EXAMPLE 41

The Bt formulation of Example 9 was evaluated in field tests for its efficacy against diamondback moth, cabbage loopers, and cabbage webworm on cabbage in Florida. The encapsulated Bt formulation was applied at 14-day intervals, and its efficacy as measured by larval counts was compared with a standard nonencapsulated Bt formulation (Cutlass WP, Ecogen Inc., Langhorne, Pa.) applied at 7-day intervals. Over the course of the one-month test in Florida, the encapsulated Bt formulation reduced the diamondback moth larvae (compared to the untreated control) by an average of 73%; it reduced the cabbage looper larvae by an average of 53%; and it reduced the cabbage webworm larvae by an average of 100%. Corresponding figures for the nonencapsulated Bt applied twice as frequently to cabbages in the same patch were 82%, 71%, and 95%, respectively. Thus, while being applied only half as often as the nonencapsulated Bt, the encapsulated Bt formulation was nearly as effective against diamondback moth and cabbage looper, and more effective against cabbage webworm.

EXAMPLE 42

The encapsulated Bt formulations of Examples 9 and 18 were evaluated in field tests for their efficacy against beet armyworm on sugar beets in California. Nonencapsulated Bt (Cutlass WP) was again used as a standard, and untreated fields were used as controls. Over a one-month period, the encapsulated formulation of Example 6 applied at 14-day intervals was nearly as effective in reducing beet armyworm larvae as was Cutlass WP applied at 7-day intervals (36% reduction in larvae vs. 46%). Over a two-week period, a single application of the encapsulated formulation of Example 15 was nearly as effective in reducing beet armyworm larvae as was Cutlass WP applied twice (44% reduction in larvae vs. 50%).

EXAMPLE 43

The encapsulated Bt formulation of Example 20 was evaluated in laboratory bioassays for its efficacy against the tobacco budworm (*Heliothis virescens*) by spraying it on garbanzo plants in a rotary turntable tower spray system. Treated and control plants were placed in a UV exposure chamber and removed at periodic intervals. Leaves from the plants were excised, placed in agar dishes and infested with 10 neonate tobacco budworm larvae. Mortality was recorded 96 hours later. Uncoated Bt particles and Dipel 2E (Abbott Laboratories, North Chicago, Ill.) Bt emulsifiable concentrate were applied similarly as standards. The efficacy of the formulations in protecting the Bt against UV degradation was measured as the number of days to decrease mortality to one-half ($t_{50}$) or one-quarter ($t_{25}$) of the initial mortality. The results are shown in the table below.

| Treatment | $t_{50}$ (days) | $t_{25}$ (days) |
|---|---|---|
| Encapsulated Bt | 4.1 | 8.1 |
| Uncoated Bt | 2.4 | 4.8 |
| Dipel 2E | 0.7 | 1.1 |

EXAMPLE 44

The encapsulated formulation of Example 25 was evaluated in field tests for its efficacy against codling moth in pears in California by applying it to pear trees at 14-day intervals; nonencapsulated CMGV was applied to pear trees in the same orchard at 7-day intervals for comparison (nonencapsulated CMGV has a known field life of 3–7 days). Both formulations were applied from a tank mix using conventional air-blast orchard sprayers. Applications were made over a two-month period. There were no significant differences in codling moth damage or market acceptability of fruit from the two different treatments, meaning that the encapsulation according to the invention provided at least an additional 7 days of field life.

EXAMPLE 45

The encapsulated formulations from Examples 27 and 29–33 were evaluated in bioassays for their efficacy against codling moth larvae by placing them and nonencapsulated CMGV standard and larval preparations (see Examples 25–37) onto a virus nutrient medium and exposing them to neonate codling moth larvae after 30 and 60 minutes of UV exposure. The number of live, dead, and moribund larvae were counted. As shown in the following table, the encapsulated formulations retained their efficacy much better than did the nonencapsulated CMGV following UV exposure.

| Ex. No. | Formulation | % Dead or Moribund 30 min UV | % Dead or Moribund 60 min UV |
|---|---|---|---|
| — | nonencapsulated std | 70 | 55 |
| — | nonencapsulated larv | 80 | 22 |
| 27 | (std) | 100 | 96 |
| 29 | (larv) | 95 | 98 |
| 30 | (std) | 98 | nm |
| 31 | (std) | 93 | 100 |
| 32 | (std) | 89 | nm |
| 33 | (std) | 93 | nm |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. In a pesticidal composition comprising
   (a) particles of pesticidal active ingredient,
   (b) a non-lignin-based pH sensitive polymer encapsulating the pesticidal active ingredient particles, and (c) a light-absorbing agent, the improvement comprising the inclusion of a lignin-based light-absorbing agent that is itself encapsulated together with said pesticidal active ingredient particles by said non-lignin-based pH-sensitive polymer, wherein said pesticidal active ingredient is a viral insecticide; said non-lignin-based pH-sensitive polymer comprises a polymer selected from cellulose acetate phthalate, polyvinyl acetate phthalate, vinyl acetate and crotonic acid copolymers, acrylic and methacrylic acids and esters, and copolymers thereof, and shellac; and said lignin-based light-absorbing agent comprises a Kraft-derived lignin, a lignin selected form sodium lignin sulfonate, calcium lignin sulfonate, sodium-calcium lignin sulfonate, carboxylated sodium lignin sulfonate, partially desulfonated lignin sulfonate, and ammonia lignin sulfonate.

2. The composition of claim 1 wherein said pesticidal active ingredient is a nuclear polyhedrosis virus..

3. The composition of claim 2 wherein said nuclear polyhedrosis virus is *Anographa falcifera*.

4. The composition of claim 1 wherein said pesticidal active ingredient is codling moth granulosis virus.

5. A pesticidal composition comprising:
  (a) a nuclear polyhedrosis virus; and
  (b) sodium lignin sulfonate wherein both (a) and (b) are encapsulated by a polymer selected from cellulose acetate phthalate, polyvinyl acetate phthalate, vinyl acetate and crotonic acid copolymers, acrylic and methacrylic acids and esters and copolymers thereof, and shellac.

6. A pesticidal composition comprising:
  (a) codling moth granulosis virus; and
  (b) sodium lignin sulfonate wherein both (a) and (b) are encapsulated by a polymer selected from cellulose acetate phthalate, polyvinyl acetate phthalate, vinyl acetate and crotonic acid copolymers, acrylic and methacrylic acids and esters and copolymers thereof, and shellac.

* * * * *

UNITED STATES PATENT AND TRADEMARK OFFICE
CERTIFICATE OF CORRECTION

PATENT NO.     : 5,750,126
DATED          : May 12, 1998
INVENTOR(S)    : Smith et al.

It is certified that error appears in the above-identified patent and that said Letters Patent is hereby corrected as shown below:

<u>Column 10,</u>
Line 1, change "larva" to read -- larv. --

Column 13, claim 2,
Line 18, delete the second period (.) after "virus."

Signed and Sealed this

Twenty-sixth Day of February, 2002

*Attest:*

JAMES E. ROGAN
*Attesting Officer*      *Director of the United States Patent and Trademark Office*